US012661204B2

(12) United States Patent
Ruegsegger et al.

(10) Patent No.: US 12,661,204 B2
(45) Date of Patent: Jun. 23, 2026

(54) HEAD FRAME PLACEMENT STABILIZATION DEVICE FOR GAMMA KNIFE RADIATION PROCEDURE

(71) Applicant: Ohio State Innovation Foundation, Columbus, OH (US)

(72) Inventors: Mark Ruegsegger, Columbus, OH (US); Megan Hart, Columbus, OH (US); Erin Foster, Columbus, OH (US); Carly Schwartz, Columbus, OH (US); Christina Keares, Columbus, OH (US); Annie Fox, Columbus, OH (US); Angela Schmalenberger, Columbus, OH (US); Vanessa Walls, Columbus, OH (US); Yazen Alfayez, Columbus, OH (US); Isaac Green, Columbus, OH (US); Taylor Kaeser, Columbus, OH (US); Lauren Riggs, Columbus, OH (US); Jacob Veney, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 95 days.

(21) Appl. No.: 18/894,926

(22) Filed: Sep. 24, 2024

(65) Prior Publication Data

US 2025/0009462 A1     Jan. 9, 2025

Related U.S. Application Data

(63) Continuation of application No. 17/728,644, filed on Apr. 25, 2022, now abandoned.

(Continued)

(51) Int. Cl.
*A61B 90/10*          (2016.01)

(52) U.S. Cl.
CPC ........ *A61B 90/10* (2016.02); *A61B 2090/101* (2016.02)

(58) Field of Classification Search
CPC ......... A61B 90/14; A61B 3/00; A61B 3/0083; A61B 2090/101; A61B 90/10; A47B 9/14; B60N 2/80; A47C 7/38; A47C 7/36
(Continued)

(56) References Cited

U.S. PATENT DOCUMENTS 3,622,233 A * 11/1971 Blood .................. A61B 3/0083
                                                    297/391
4,431,279 A * 2/1984 Morohashi ........... A61B 3/0008
                                                    351/221

(Continued)

FOREIGN PATENT DOCUMENTS

WO          2009129847          10/2009

OTHER PUBLICATIONS

Brain Stereotactic Radiosurgery—Mayo Clinic. Retrieved Dec. 7, 2020, from https://www.mayoclinic.org/tests-procedures/brain-stereotactic-radiosurgery/about/pac-20384679.
(Continued)

*Primary Examiner* — Christopher Garft
(74) *Attorney, Agent, or Firm* — Meunier Carlin & Curfman LLC

(57)          ABSTRACT
Various implementations include a head frame holding device. The device includes a base, a head rest, and at least one head frame holder. The head rest has a first end coupled to the base and a second end spaced apart from the first end. The at least one head frame holder has a first end coupled to the base and a second end spaced apart from the first end. The second end of the at least one head frame holder includes a head frame coupler for coupling the head frame to the device.

19 Claims, 3 Drawing Sheets

Related U.S. Application Data

(60) Provisional application No. 63/178,906, filed on Apr. 23, 2021.

(58) Field of Classification Search
USPC .......................................................... 248/118
See application file for complete search history.

(56) References Cited

U.S. PATENT DOCUMENTS

| | | | | |
|---|---|---|---|---|
| 5,000,563 | A * | 3/1991 | Gisel ................... | A61B 3/0083 |
| | | | | 351/244 |
| 2007/0007400 | A1* | 1/2007 | James ...................... | A61G 7/05 |
| | | | | 297/423.12 |
| 2007/0040482 | A1* | 2/2007 | Williams ............... | A47B 29/00 |
| | | | | 312/21 |
| 2016/0270650 | A1* | 9/2016 | Norwood ............. | A61B 3/0083 |
| 2019/0209070 | A1* | 7/2019 | Cherchi ............... | A61B 5/4082 |

OTHER PUBLICATIONS

Gamma Knife for Cancer—Abramson Cancer Center. Penn Medicine. Retrieved Dec. 8, 2020, from https://www.pennmedicine.org/cancer/navigating-cancer-care/treatmenttypes/radiation/gamma-knife.

Gamma Knife | Conditions & Treatments | UCSF Health. Retrieved Dec. 7, 2020, from https://www.ucsfhealth.org/treatments/gamma-knife.

Other Brain Cancers Treatment. The James The Ohio State University Comprehensive Cancer Center. Retrieved Dec. 9, 2020, from https://cancer.osu.edu/for-patientsand-caregivers/learn-about-cancers-and-treatments/cancers-conditions-andtreatment/cancer-types/other-brain-cancers/treatment.

What to Expect from Gamma Knife Treatment. RWJUH New. Retrieved Dec. 8, 2020, from https://www.rwjbh.org/rwj-university-hospital-new-brunswick/treatmentcare/gamma-knife/what-to-expect/.

Medtronic. DBS For Parkinson's Disease | DBS Surgery. Medtronic. Retrieved Dec. 7, 2020, from https://www.medtronic.com/us-en/patients/treatments-therapies/deep-brainstimulation-parkinsons-disease/about-dbs-therapy/dbssurgery.html?cmpid=PPC_Bing_Q1_XTPDTreatment_H11_WhtIsDBSSrgry_H12_FndDocNearU2Ask_H13_InfoGivsClosrLook_D1_ExplorDBSByTlkWthDocNearbyWhoCnPrvdRelableInfo_D2_EntrZipCod2FndDOcWhoKnwsAbtDBS_RTG_DBS_Parkinsons_FY21&ef_id=c16f817f718d1bfa5424deblb60982ce:G:s&skwcid=AL!5660!10!82257451896610!82257632354742&msclkid=c16f817f718d1bfa5424deb1b60982ce.

Safaee M, Burke J, Mcdermott M W. (Mar. 25, 2016) Techniques for the Application of Stereotactic Head Frames Based on a 25-Year Experience. Cureus 8(3): e543. DOI10.7759/cureus.543.

Payne, B., Weber, J. and Payne, M., 2007. A Split Strap Frame Applicator For Stereotactic Frame Placement. Surgical Neurology. [online] pp. 684-685. Available at: <https://www.sciencedirect.com/science/article/abs/pii/S0090301907001231>.

Nakazawa, H., 2014. Useful Base Plate To Support The Head During Leksell Skull Frame Placement In Gamma Knife Perfexion Radiosurgery. [online] Department of Radiological Sciences, Nagoya University Graduate School of Medicine. Available at:https://www.med.nagoyau.ac.jp/medlib/nagoya_j_med_sci/7612/04_Nakazawa.pdf>.

Commissioner, Office of the. "What We Do." U.S. Food and Drug Administration, FDA, www.fda.gov/about-fda/what-we-do.

* cited by examiner

HEAD FRAME PLACEMENT STABILIZATION DEVICE FOR GAMMA KNIFE RADIATION PROCEDURE

CROSS-REFERENCE TO RELATED APPLICATIONS

This application is a continuation of U.S. Non-Provisional patent application Ser. No. 17/728,644, filed Apr. 25, 2022, which claims the benefit of U.S. Provisional Patent Application Ser. No. 63/178,906, filed Apr. 23, 2021. All of the aforementioned applications are hereby incorporated by reference herein in their entireties and for all purposes.

BACKGROUND

Patients that have tumors, vascular deformities, or other abnormalities in the brain are primarily treated with gamma knife radiation therapy as a safer alternative to standard brain surgeries. This non-invasive radiation surgery is one of the most advanced and highly sought-after treatments for brain-related conditions. It allows for the radiation doses to precisely target one specific area in the brain, while leaving the healthy tissue that surrounds that area untouched. The precision of this radiation therapy is critical. Therefore, a stereotactic headframe is used as a stabilization device for the patient during treatment. Consequently, it is imperative that the process of placing this stereotactic head frame on to the patient's head is as effective as possible, allowing for the prioritization of the safety and comfort of the patient, as well as the healthcare team. In order to achieve this, the patient's head and the head frame itself must remain stable during this placement process. Currently, assistive nurses act to stabilize both the patient's head and the head frame for the entire duration of this placement process, which can take up to 30 minutes. These nurses must account for many different factors during this process, including remaining as stable as possible so to not cause the patient any harm, as well as staying out of the surgeon's way while the pins are being screwed in place.

In some current procedures, an oncology nurse sits behind the patient and holds the patient's head by putting their hands through an opening in the fiducial box attached to the head frame. The head frame placement procedure takes anywhere from 15 to 30 minutes and can be performed with the patient either under light sedation or general anesthesia. This impacts the nurse because the patient is no longer able to help in the stabilization of their head, which puts more strain on the nurse and creates more risk for the patient. Nurses have reported chronic pain and joint damage as a result of the current head frame placement procedure.

There are a number of stabilization devices commercially available that can be used during this head frame placement procedure. These devices use the patient's head in order to stabilize the frame, but a second person must be behind the patient holding the frame still in order to stop the frame from rotating. Such stabilization devices have been used in the United States for over twenty-five years.

Another notable device utilizes hook-and-loop fastener straps in order to stabilize the frame on the patient's head. The hook-and-loop fastener acts as a split strap that holds the weight of the frame while ear bars are used to orient the frame and keep the patient's head steady within the frame. These devices wrap around the top of the patient's head and the hook-and-loop fastener fastens around the sides of the frame in order to keep it stable. Additionally, the strap counteracts the force from screwing the headframe in place and relieves some of the pain that the patient feels from the ear bars.

Another device is a non-invasive face mask that replaces the fixed head frame. These masks do not require the use of sedation or the use of screws. The masks are made of thermoplastic sheets, and once heated, are placed on the patient's head such that the plastic cools and forms around the patient head allowing for accurate placement.

However, these current devices do not take into account the fiducial box that needs to be attached to the headframe during the placement procedure. Most of these devices still require a nurse to hold the patient's head upright. Furthermore, the non-invasive head frame interferes with the gamma knife procedure and is not currently compatible with gamma knife machine.

Thus, there is a need for a stabilization device that acts to hold the full weight of the patient's head, as well as the head frame, is our proposed solution.

BRIEF DESCRIPTION OF THE DRAWINGS

Example features and implementations are disclosed in the accompanying drawings. However, the present disclosure is not limited to the precise arrangements and instrumentalities shown.

DETAILED DESCRIPTION

Figure 2:
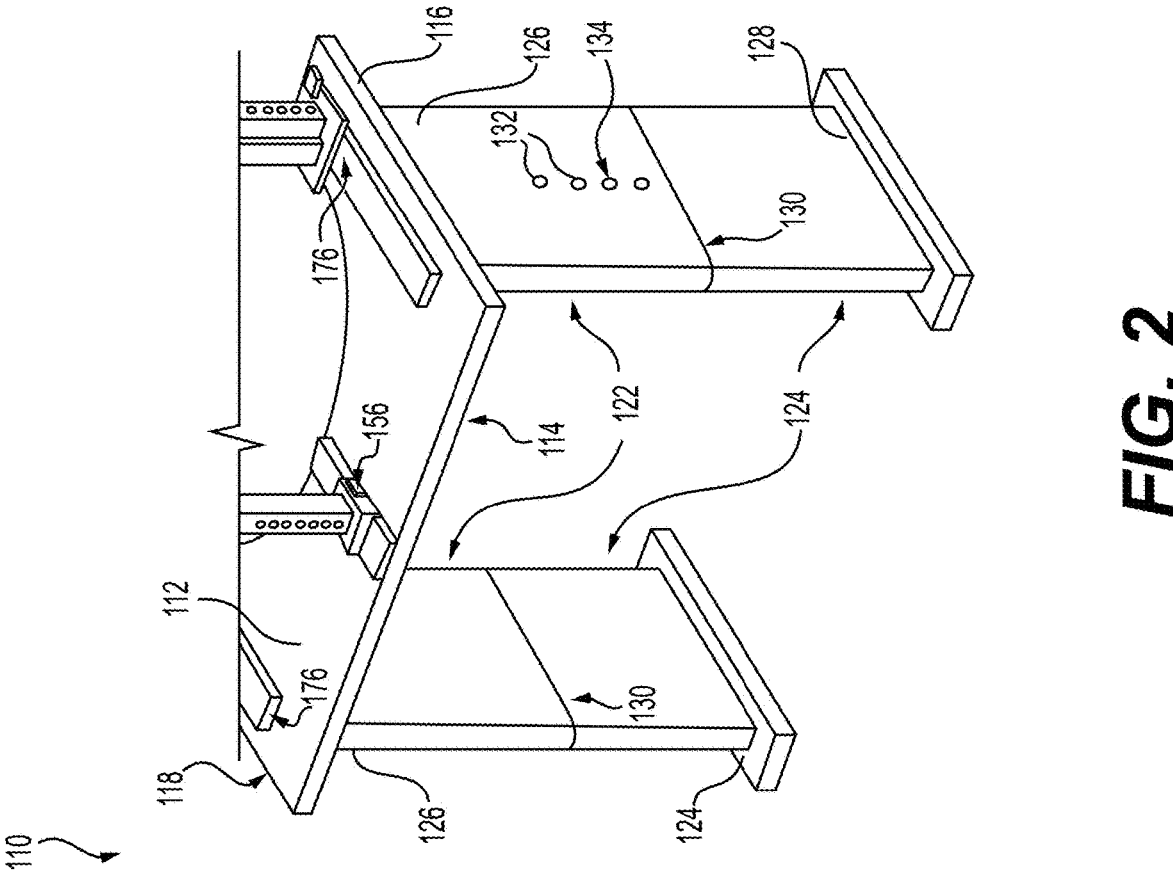
FIG. 2 shows a detailed perspective view of the base and legs of the device shown in FIG. 1.

The devices, systems, and methods disclosed herein provide for a stabilization device that holds the full weight of a patient's head and a gamma knife headframe. The device stabilizes the patient's head and the gamma knife headframe during a gamma knife radiation procedure. Placing the headframe onto the patient's head is one of the key components of gamma knife radiation therapy, and possibly the most painful step in the entire procedure for the patients. It is important that there is a standard procedure for this process to not only ensure that it is done effectively each time, but to also reduce the number of times the headframe has to be repositioned. The disclosed devices minimize the dependency on the nurse in the current procedure for head frame placement. The disclosed devices hold the aforementioned head frame around the patient's head while ensuring the patient's head remains steady for the procedure. While the example of the disclosed devices herein focus on utilization during gamma knife radiation procedures, in other implementations, the devices are used for the process of deep brain stimulation or any other procedure that requires a patient's head be supported and steady.

Gamma knife surgery is a radiation treatment used to address small yet fatal abnormalities in the brain. One of the most common conditions treated with gamma knife radiation therapy is cancer metastasis. An unprecedented amount of precision is needed in order for this treatment to be effective, presenting the need for the patient to be fully stabilized during radiation treatment. The placement of a stereotactic head frame on the patient is utilized to act as this stabilizing device. The head frame is attached to the patient's head using metal screws which pierce the skin of the forehead and the back of the scalp. In order to place the head frame in a precise manner, both the head frame and the patient's head must be held still throughout the placement procedure.

The disclosed devices are primarily targeted for patients receiving gamma knife radiation therapy, however it can be used for treating the entanglement of blood vessels and aggressive brain cancer, also.

The main goal of the new assistive device is to improve upon the current process of placing the radiation head frame on the patient. First, the device is stable so the head frame does not move during the placement process. This is important to the device's function as patient safety and device effectiveness depends on frame stability. The device is also adaptable to not only a variety of patient sizes but to patients in wheelchairs as well. This allows the device to accommodate a variety of patients that may require the procedure. The device is constructed of materials that can be easily cleaned without requiring disassembly for disinfection. Finally, the device creates a standardization of the placement process that did not previously exist.

One constraint of the device stems from the radiation head frame itself. Since the head frame is standard to the machine completing the procedure, no adjustments can be made to its design. The device attaches to the existing frame without adding any parts or attachment mechanisms to the head frame. It attaches in a location that does not block or obstruct the areas which the medical personnel need to access during the process. This includes but is not limited to the pin holes which are used to attach rods to the patient's head. Lastly, the device does not inhibit the nurses' ability to stabilize the patient's body as the device is meant to stabilize just the head frame.

Also, as discussed above, the gamma knife procedure can be done in two different positions: the patient laying in a bed or the patient sitting in a chair. To accommodate both positions, the disclosed devices are able to attach to either a bed frame or a chair frame for successful head frame placement in either position. The device itself is further adjustable based on the patient. Different patients will differ in size and height and therefore require the device to adjust accordingly.

The device includes materials that are able to be wiped down with antibacterial wipes or any other cleaning process the hospital uses. Furthermore, in some implementations, the material of the device that contacts the patient's head is hypoallergenic and comfortable. Also, any portions of the device interacting with the patient's head that are weight or load bearing are padded to ensure the patient stays comfortable.

In some implementations, the device includes a lap desk that hold up a plurality of supports. The lap desk includes a rigid horizontal table piece that will be set either on a patient's lap or arms of a chair. This table acts as the base of the entire support device, and since it is the baseline for the supports and has the ability to be placed on either the arms of the chair or patient's lap, the table also can be adjusted based on the patient's size, position, and comfort preference. The device includes three supports held up by the table. The middle support includes a chin rest that holds the weight of the patient's head. This piece will both hold the entire weight of the head as well as stabilize the head, removing this burden from the nurses. The chin rest is a similar shape to that of a chin rest at an optometry office and is adjustable in the z-direction to allow for patient variability. The other two supports are on either side of the middle support and include clamps that are disposed on an end of the other two supports opposite the table. These other two supports carry the weight of the head frame as well as stabilize the head frame. Similar to the chin rest, these supports will also be adjustable in the z-direction to account for patient variability. Each of the plurality of supports are mounted to the same base, providing stabilization to each part relative to others (i.e., the head will be stabilized relative to the head frame since the supports come from the same piece).

Various implementations include ahead frame holding device. The device includes a base, a head rest, and at least one head frame holder. The head rest has a first end coupled to the base and a second end spaced apart from the first end. The at least one head frame holder has a first end coupled to the base and a second end spaced apart from the first end. The second end of the at least one head frame holder includes a head frame coupler for coupling the head frame to the device.

FIGS. 1-6 show a head frame holding device 100, according to aspects of various implementations. The device 100 includes a base 110, a head rest 140, and two head frame holders 160.

The base 110, shown in FIG. 2, is a platform having a first surface 112, a second surface 114 opposite and spaced apart from the first surface 112, a first edge 116 extending between the first surface 112 and the second surface 114, and a second edge 118 opposite and spaced apart from the first surface 112. The base 110 acts as a reference point with respect to which all other features of the device 100 are kept motionless.

The base 110 includes two legs 120 extending from the base 110. Each of the two legs 120 include a first portion 122 having a first end 126 of the leg 120 and a second portion 124 having a second end 128 of the leg 120. The first end 126 of the leg 120 is coupled to the second surface 114 of the base 110, and the second end 128 of the leg 120 is spaced apart from the first end 126 of the leg 120.

The first portion 122 of the leg 120 defines a central longitudinal opening 130 and the second portion 124 of the leg 120 is slidingly disposed within the central longitudinal opening 130 of the leg 120. The side wall of the first portion 122 of the leg 120 defines a plurality of side openings 132. The second portion 124 of the leg 120 includes one spring loaded locking pin 134 that is selectively disposable within one of the side openings 132 of the leg 120. The locking pin 134 of the leg 120 can be depressed below the inner surface of the first portion 122 of the leg 120 to allow the second portion 124 of the leg 120 to be slidingly moved relative to the first portion 122 of the leg 120. When the locking pin 134 of the leg 120 reaches another side opening 132 of the first portion 122 of the leg 120, the bias from the spring force of the locking pin 134 of the leg 120 pushes the locking pin 134 of the leg 120 through the side opening 132 of the leg 120 to rigidly couple the first portion 122 of the leg 120 to the second portion 124 of the leg 120.

As mentioned above, because the second portion 124 of each of the legs 120 is telescopingly disposed within the central longitudinal opening 130 of the first portion 122 of the leg 120, the second end 128 of the leg 120 is slidingly movable relative to the first end 126 of the leg 120. The second end 128 of the leg 120 can be moved between a first position to a second position. The second end 128 of the leg 120 is closer to the first end 126 of the leg 120 in the first position than in the second position. This adjustability of the overall length of the legs 120 allows the device 100 to be used comfortably and effectively by users of different sizes.

Figure 1:
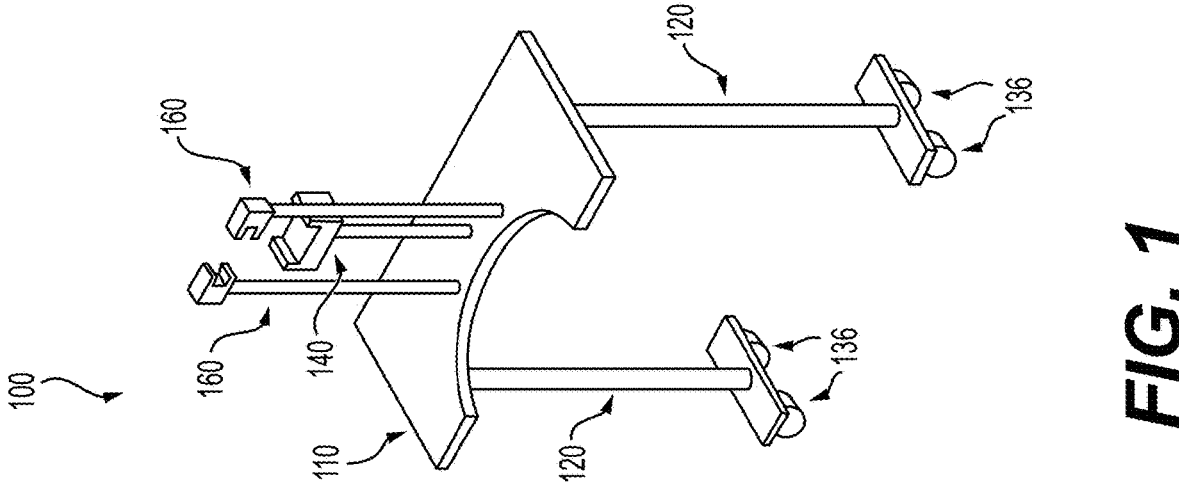
FIG. 1 shows a perspective view of a head frame holding device, according to one implementation.

As shown in FIG. 1, each of the legs 120 can include wheels 136 to allow the device 100 to be used by a user who is in the standing position. The one or more wheels 136 allow the device 100 to be easily maneuvered into the correct position.

In some implementations, the first edge and the second edge of the base each include an attachment clasp extending from their respective edges of the base. Each of the two attachment clasps include a portion extending substantially perpendicular to a longitudinal axis of the head rest. The attachment clasps are configured such that when a user is sitting in a chair with arms, each of the attachment clasps can rest on a different one of the arms of the chair while the base is disposed in the user's lap. The attachment clasps can include coupling portions to help secure the base to the chair. For example, the attachment clasps can include hooking portions at their distal ends that prevent the base from shifting laterally across the arms of the chair. In some implementations, the attachment clasps can include clamps, adhesives, or any other attachment mechanisms to allow the base to be secured to the arms of the chair during use.

Although the device 100 shown in FIGS. 1-6 includes two legs 120, in other implementations, the device can include two or more legs. In some implementations, the second portion of the leg can include the central longitudinal opening, and the first portion of the leg can be slidingly disposed within the central longitudinal opening of the second portion of the leg. In some implementations, the second portion of the leg can define the side openings, and the first portion of the leg can include the locking pins. In some implementations, the locking pins can be removable pins that are not included in either the first portion of the leg or the second portion of the leg. In some implementations, the adjustability of the legs can be done by any other adjustability mechanism known in the art.

Figure 3:
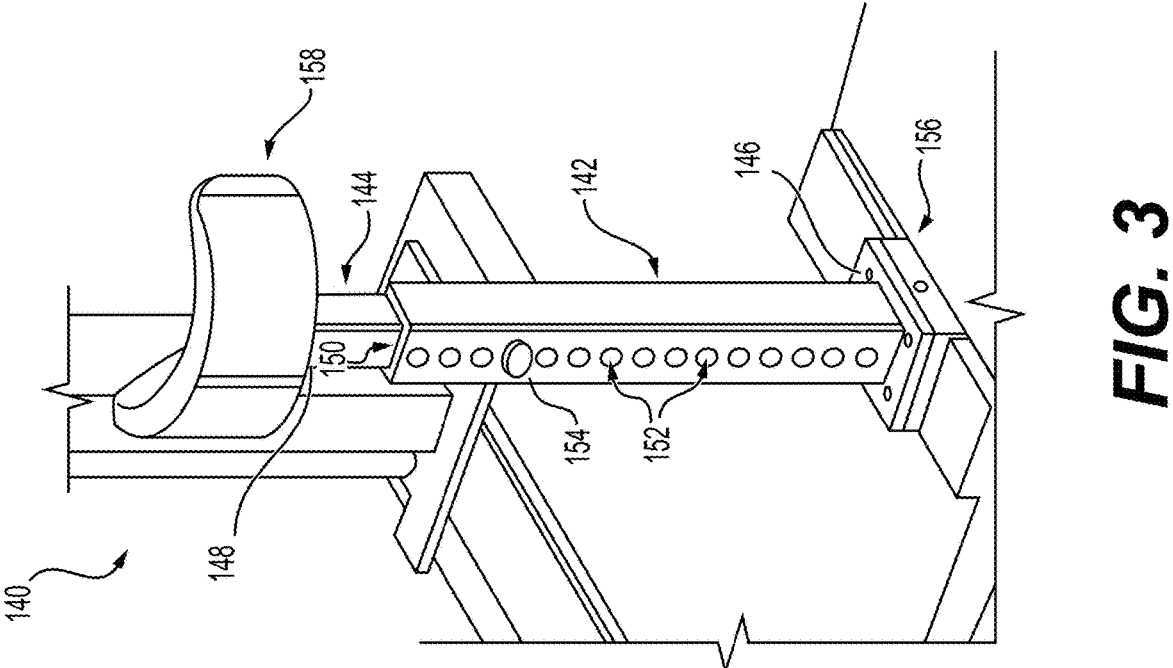
FIG. 3 shows a detailed perspective view of the head rest of the device of FIG. 1.

The head rest 140, shown in FIG. 3, is used to stabilize the position of the user's head relative to the base 110. The head rest 140 includes a first portion 142 and a second portion 144. The first portion 142 of the head rest 140 has a first end 146 slidingly coupled to the first surface 112 of the base 110 by a rail and bearing 156, and the second portion 1144 of the head rest 140 has a second end 148 spaced apart from the first end 146. The second end 148 of the head rest 140 includes a chin rest 158 that defines a concave surface facing opposite from the first end 146 of the head rest 140. The concave surface of the chin rest 158 also includes a cushion. The user can place his/her chin on the cushion of the concave surface of the chin rest 158 to stabilize the user's head relative to the base 110.

The first portion 142 of the head rest 140 defines a central longitudinal opening 150 and the second portion 144 of the head rest 140 is slidingly disposed within the central longitudinal opening 150 of the head rest 140. The side wall of the first portion 142 of the head rest 140 defines a plurality of side openings 152. The second portion 144 of the head rest 140 includes one spring loaded locking pin 154 that is selectively disposable within one of the side openings 152 of the head rest 140. The locking pin 154 of the head rest 140 can be depressed below the inner surface of the first portion 142 of the head rest 140 to allow the second portion 144 of the head rest 140 to be slidingly moved relative to the first portion 142 of the head rest 140. When the locking pin 154 of the head rest 140 reaches another side opening 152 of the first portion 142 of the head rest 140, the bias from the spring force of the locking pin 154 of the head rest 140 pushes the locking pin 154 of the head rest 140 through the side opening 152 of the head rest 140 to rigidly couple the first portion 142 of the head rest 140 to the second portion 144 of the head rest 140.

As mentioned above, because the second portion 144 of the head rest 140 is telescopingly disposed within the central longitudinal opening 150 of the first portion 142 of the head rest 140, the second end 148 of the head rest 140 is slidingly movable relative to the first end 146 of the head rest 140. The second end 148 of the head rest 140 can be moved between a first position to a second position. The second end 148 of the head rest 140 is closer to the first end 146 of the head rest 140 in the first position than in the second position. This adjustability of the overall length of the head rest 140 allows the device 100 to be used comfortably and effectively by users of different sizes.

In some implementations, the second portion of the head rest can include the central longitudinal opening, and the first portion of the head rest can be slidingly disposed within the central longitudinal opening of the second portion of the head rest. In some implementations, the second portion of the head rest can define the side openings, and the first portion of the head rest can include the locking pins. In some implementations, the locking pins can be removable pins that are not included in either the first portion of the head rest or the second portion of the head rest. In some implementations, the adjustability of the head rest can be done by any other adjustability mechanism known in the art.

Figure 4:
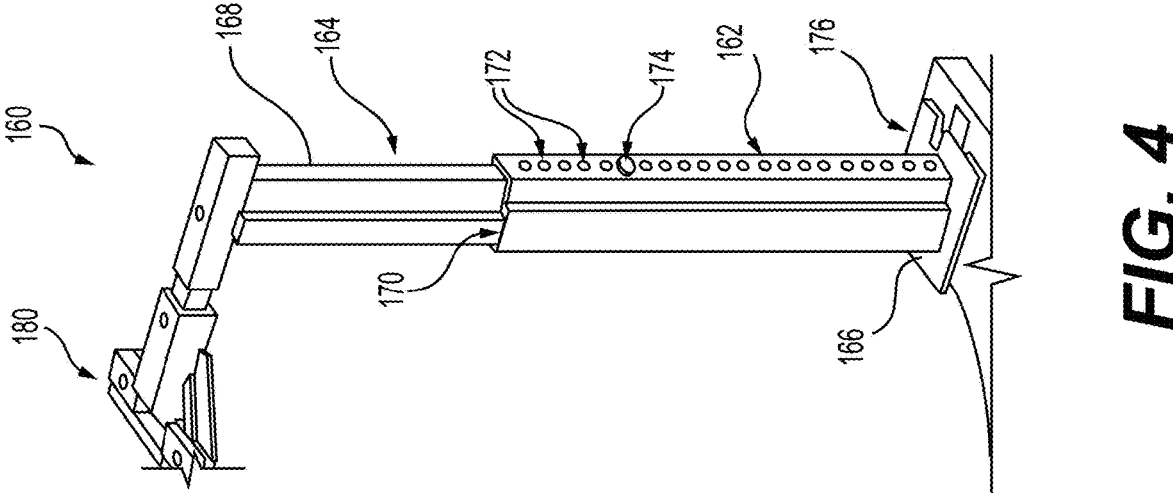
FIG. 4 shows a detailed perspective view of the head frame holder of the device of FIG. 1.
Figures 5, 6:
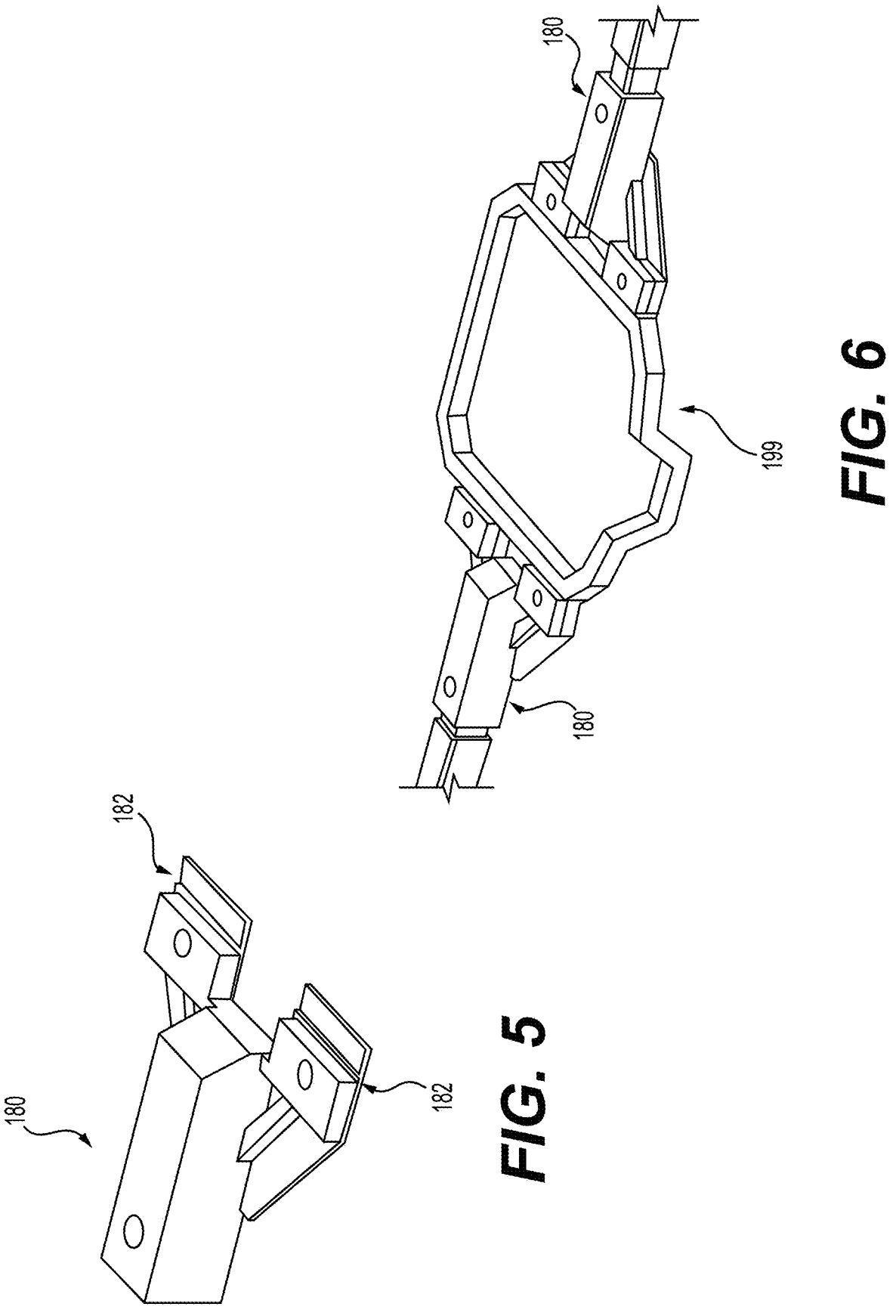
FIG. 5 shows a detailed perspective view of the head frame clamp of the head frame holder of the device shown in FIG. 1.
FIG. 6 shows a detailed perspective view of the head frame clamps of the device of FIG. 1 coupled to a head frame.

The device 100 includes a first head frame holder 160 and a second head frame holder 160, as shown in FIGS. 1, 4, and 6. As shown in FIG. 4, each head frame holder 160 has a first portion 162 and a second portion 164. The first portion 162 of each head frame holder 160 has a first end 166 slidingly coupled to the first surface 112 of the base 110 by a rail and bearing 176, and the second portion 164 of the head frame holder 160 has a second end 168 spaced apart from the first end 166 of the head frame holder 160. The second end 168 of each head frame holder 160 includes a head frame coupler 180 that is configured to couple to a head frame 199 such that the head frame 199 is coupled to the device 100.

As seen in FIG. 4, the first portion 162 of each of the head frame holder 160 defines a central longitudinal opening 170 and the second portion 164 of the head frame holder 160 is slidingly disposed within the central longitudinal opening 170 of the head frame holder 160. The side wall of the first portion 162 of the head frame holder 160 defines a plurality of side openings 172. The second portion 164 of the head frame holder 160 includes one spring loaded locking pin 174 that is selectively disposable within one of the side openings 172 of the head frame holder 160. The locking pin 174 of the head frame holder 160 can be depressed below the inner surface of the first portion 162 of the head frame holder 160 to allow the second portion 164 of the head frame holder 160 to be slidingly moved relative to the first portion 162 of the head frame holder 160. When the locking pin 174 of the head frame holder 160 reaches another side opening 172 of the first portion 162 of the head frame holder 160, the bias from the spring force of the locking pin 174 of the head frame holder 160 pushes the locking pin 174 of the head frame holder 160 through the side opening 172 of the head frame holder 160 to rigidly couple the first portion 162 of the head frame holder 160 to the second portion 164 of the head frame holder 160.

As mentioned above, because the second portion 164 of each of the head frame holders 160 is telescopingly disposed within the central longitudinal opening 170 of the first portion 162 of the head frame holder 160, the second end 168 of the head frame holder 160 is slidingly movable relative to the first end 166 of the head frame holder 160. The second end 168 of the head frame holder 160 can be moved between a first position to a second position. The second end 168 of the head frame holder 160 is closer to the first end 166 of the head frame holder 160 in the first position than in the second position. This adjustability of the overall length of the head frame holder 160 allows the device 100 to be used comfortably and effectively by users of different sizes.

As shown in FIGS. 5 and 6, each of the head frame couplers 160 includes a head frame clamp 180 coupled to the second end 168 of the head frame holder 160. The head frame clamp 180 includes a protrusion 182 that is configured to be disposed within a groove of a head frame 199. Each of the two head frame clamps 180 is slidingly coupled to the second end 168 of a different one of the head frame holders 160 such that the head frame clamps 180 can be moved toward and away from each other.

Although the device 100 shown in FIGS. 1-6 includes two head frame holders 160, in other implementations, the device can include one or more head frame holders. In some implementations, the second portion of the head frame holders can include the central longitudinal opening, and the first portion of the head frame holders can be slidingly disposed within the central longitudinal opening of the second portion of the head frame holders. In some implementations, the second portion of the head frame holders can define the side openings, and the first portion of the head frame holders can include the locking pins. In some implementations, the locking pins can be removable pins that are not included in either the first portion of the head frame holders or the second portion of the head frame holders. In some implementations, the adjustability of the head frame holders can be done by any other adjustability mechanism known in the art.

In use, the head frame holders 160 are adjusted to the rough height of the patient's head while seated. The head frame 199 is then placed onto the protrusions 182 of the head frame couplers 180. The head frame couplers 180 can be adjusted toward or away from each other to accommodate different sized frames 199.

Once the frame 199 is placed in the head frame clamps 180 of the head frame holders 160, the head frame clamps 180 are tightened down to secure the head frame 199 to the device 100 and to ensure that the head frame 199 does not shift or slide throughout the process. This design allows for the best griping method without obstruction of sightlines while simultaneously providing support to the head frame 199.

Once the patient's head is placed within the head frame 199, the head rest 140 can be adjusted such that the chin rest 158 contacts the patient's chin. The legs 120 of the device 100 can then be adjusted to a height that is comfortable for the patient.

The modular design of the device 100 allows the device 100 to be easily broken down into specific modular or interchangeable components for ease of cleaning, development, and customizability. Each segment is connected by a standardized method, be it linear rail or aluminum extrusion that allows for attachment and modification.

A number of example implementations are provided herein. However, it is understood that various modifications can be made without departing from the spirit and scope of the disclosure herein. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. Although the terms "comprising" and "including" have been used herein to describe various implementations, the terms "consisting essentially of" and "consisting of" can be used in place of "comprising" and "including" to provide for more specific implementations and are also disclosed.

Disclosed are materials, systems, devices, methods, compositions, and components that can be used for, can be used in conjunction with, can be used in preparation for, or are products of the disclosed methods, systems, and devices. These and other components are disclosed herein, and it is understood that when combinations, subsets, interactions, groups, etc. of these components are disclosed that while specific reference of each various individual and collective combinations and permutations of these components may not be explicitly disclosed, each is specifically contemplated and described herein. For example, if a device is disclosed and discussed each and every combination and permutation of the device are disclosed herein, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed systems or devices. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

What is claimed is:

1. A head frame holding device, the device comprising:
a base;
a head rest having a first end coupled to the base and a second end spaced apart from the first end; and
at least one head frame holder having a first end coupled to the base and a second end spaced apart from the first end, wherein the second end of the at least one head frame holder includes a head frame coupler for coupling a head frame to the device;
wherein the head frame coupler includes at least one head frame clamp coupled to the second end of the at least one head frame holder, wherein the at least one head frame clamp includes a protrusion that is configured to be disposed within a groove of a head frame.

2. The device of claim 1, wherein the second end of the head rest includes a chin rest.

3. The device of claim 2, wherein the chin rest includes a concave surface facing opposite from the first end of the head rest.

4. The device of claim 2, wherein the chin rest includes a cushion.

5. The device of claim 1, wherein the second end of the head rest can be moved between a first position to a second position, wherein the second end of the head rest is closer to the first end of the head rest in the first position than in the second position.

6. The device of claim 5, wherein the head rest includes a first portion including the first end of the head rest and a second portion including the second end of the head rest, wherein one of the first portion of the head rest or the second portion of the head rest defines a central longitudinal opening, and an other of the second portion of the head rest or first portion of the head rest is slidingly disposed within the central longitudinal opening of the head rest.

7. The device of claim 6, wherein the one of the first portion of the head rest or the second portion of the head rest defines one or more side openings, the head rest further including one or more locking pins disposable within the one or more side openings of the head rest to rigidly couple the first portion of the head rest to the second portion of the head rest.

8. The device of claim 1, wherein the first end of the head rest is slidingly coupled to the base by a rail and bearing.

9. The device of claim 1, wherein the at least one head frame holder includes two head frame holders.

10. The device of claim 1, wherein the second end of the at least one head frame holder can be moved between a first position to a second position, wherein the second end of the at least one head frame holder is closer to the first end of the at least one head frame holder in the first position than in the second position.

11. The device of claim 10, wherein the at least one head frame holder includes a first portion including the first end of the at least one head frame holder and a second portion including the second end of the at least one head frame holder, wherein one of the first portion of the at least one head frame holder or the second portion of the at least one head frame holder defines a central longitudinal opening, and an other of the second portion of the at least one head frame holder or first portion of the at least one head frame holder is slidingly disposed within the central longitudinal opening of the at least one head frame holder.

12. The device of claim 11, wherein the one of the first portion of the at least one head frame holder or the second portion of the at least one head frame holder defines one or more side openings, the at least one head frame holder further including one or more locking pins disposable within the one or more side openings of the at least one head frame holder to rigidly couple the first portion of the at least one head frame holder to the second portion of the at least one head frame holder.

13. The device of claim 1, wherein the first end of the at least one head frame holder is slidingly coupled to the base by a rail and bearing.

14. The device of claim 1, further comprising at least two legs extending from the base, wherein the at least two legs have a first end coupled to the base and a second end spaced apart from the first end of the at least two legs.

15. The device of claim 14, wherein the second end of the at least two legs can be moved between a first position to a second position, wherein the second end of the at least two legs is closer to the first end of the at least two legs in the first position than in the second position.

16. The device of claim 15, wherein the at least two legs include a first portion including the first end of the at least two legs and a second portion including the second end of the at least two legs, wherein one of the first portion of the at least two legs or the second portion of the at least two legs defines a central longitudinal opening, and an other of the second portion of the at least two legs or the first portion of the at least two legs is slidingly disposed within the central longitudinal opening of the at least two legs.

17. The device of claim 16, wherein the one of the first portion of the at least two legs or the second portion of the at least two legs defines one or more side openings, the of the at least two legs further including one or more locking pins disposable within the one or more side openings of the at least two legs to rigidly couple the first portion of the at least two legs to the second portion of the at least two legs.

18. The device of claim 14, wherein the at least two legs each include two or more wheels coupled the second end of each of the at least two legs.

19. The device of claim 1, wherein the at least one head frame clamp includes two head frame clamps, wherein the at least one head frame holder includes two head frame holders, wherein each of the two head frame clamps is slidingly coupled to the second end of a different one of the head frame holders such that the head frame clamps can be moved toward and away from each other.

* * * * *